(12) United States Patent
Dasbach et al.

(10) Patent No.: US 9,694,143 B2
(45) Date of Patent: Jul. 4, 2017

(54) NEEDLE ASSEMBLY ATTACHMENT AND REMOVAL DEVICE

(71) Applicant: SANOFI-AVENTIS DEUTSCHLAND GMBH, Frankfurt am Main (DE)

(72) Inventors: Uwe Dasbach, Frankfurt am Main (DE); Christoph Dette, Frankfurt am Main (DE); Peter Nober, Rommersheim (DE); Fiete Sonntag, Ahaus (DE); Christoph Eisengarthen, Ginsheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 631 days.

(21) Appl. No.: 14/360,276

(22) PCT Filed: Nov. 23, 2012

(86) PCT No.: PCT/EP2012/073465
§ 371 (c)(1),
(2) Date: May 22, 2014

(87) PCT Pub. No.: WO2013/076244
PCT Pub. Date: May 30, 2013

(65) Prior Publication Data
US 2014/0276443 A1    Sep. 18, 2014

(30) Foreign Application Priority Data
Nov. 24, 2011 (EP) .................................... 11190581

(51) Int. Cl.
*A61M 5/00* (2006.01)
*A61M 5/34* (2006.01)
*A61M 5/32* (2006.01)

(52) U.S. Cl.
CPC .......... *A61M 5/344* (2013.01); *A61M 5/3276* (2013.01); *A61M 5/347* (2013.01); *A61M 2005/3208* (2013.01)

(58) Field of Classification Search
CPC ........ A61M 2005/3208; A61M 5/3205; A61M 5/3276; A61M 2005/3215; A61M 5/343; A61M 5/347
See application file for complete search history.

(56) References Cited

U.S. PATENT DOCUMENTS

| 4,986,811 A | * | 1/1991 | Thead | A61M 5/3205 206/366 |
| 4,989,307 A | * | 2/1991 | Sharpe | A61M 5/3205 128/917 |

(Continued)

FOREIGN PATENT DOCUMENTS

| WO | 2010113388 A1 | 10/2010 | |
| WO | WO 2010113388 A1 * | 10/2010 | A61M 5/3205 |
| WO | 2010124974 A2 | 11/2010 | |

*Primary Examiner* — Andrew Gilbert
*Assistant Examiner* — William Carpenter
(74) *Attorney, Agent, or Firm* — Fish & Richardson P.C.

(57) ABSTRACT

Described is a needle assembly attachment and removal device comprising a case having a base and a longitudinal axis (L), a carriage axially movable with the case from a first position to a second position, a carrier rotatably coupled to the carriage and adapted to hold a needle assembly, and a gearing arrangement rotatably coupled to the carriage and adapted to rotate the carrier in a first rotational direction as the carriage moves from the first position to the second position and in a second rotational direction as the carriage moves from the second position to the first position.

20 Claims, 5 Drawing Sheets

(56) References Cited

U.S. PATENT DOCUMENTS

| | | | | |
|---|---|---|---|---|
| 5,188,598 A | * | 2/1993 | Thead | A61M 5/3205 |
| | | | | 206/366 |
| 5,312,346 A | * | 5/1994 | Han | A61M 5/3205 |
| | | | | 206/365 |
| 5,573,113 A | * | 11/1996 | Shillington | A61M 5/3205 |
| | | | | 206/366 |
| 5,741,230 A | * | 4/1998 | Miller | A61L 11/00 |
| | | | | 219/68 |
| 5,791,471 A | * | 8/1998 | Radmand | A61C 19/00 |
| | | | | 206/366 |
| 5,947,950 A | | 9/1999 | Shillingston et al. | |
| 9,283,328 B2 | * | 3/2016 | Dasbach | A61M 5/3276 |
| 2005/0121343 A1 | * | 6/2005 | Miller | A61M 5/3205 |
| | | | | 206/366 |
| 2005/0288636 A1 | * | 12/2005 | Gerald Cooley | A61M 5/3205 |
| | | | | 604/187 |

\* cited by examiner

NEEDLE ASSEMBLY ATTACHMENT AND REMOVAL DEVICE

CROSS REFERENCE TO RELATED APPLICATIONS

The present application is a U.S. National Phase application pursuant to 35 U.S.C. §371 of International Application No. PCT/EP2012/073465 filed Nov. 23, 2012, which claims priority to European Patent Application No. 11190581.6 filed Nov. 24, 2011. The entire disclosure contents of these applications are herewith incorporated by reference into the present application.

FIELD OF INVENTION

The invention relates to a needle assembly attachment and removal device for attaching a needle assembly to and removing a needle assembly from a medicament delivery device.

BACKGROUND

Administering a medicament by injection is a process which presents a number of risks and challenges for patients and healthcare professionals, both mental and physical. Improper handling of medicament delivery devices may result in needle stick injuries. In any situation in which a patient or healthcare professional is required to manually attach/remove the needle assembly, there is a risk of needle stick injury.

In addition, manually attaching the needle assembly to the medicament delivery device can lead to over-tightening, which can result in injury when removing the needle assembly and/or structural damage to the medicament delivery device. Attempts to remove an over-tightened needle assembly can adversely affect other components of the medicament delivery device (e.g., in a reusable device, a cartridge holder may be loosened).

Further, manually attaching the needle assembly may lead to mismatch of screw threads, resulting in an obliquely-oriented needle. This may lead to a defective septum or to an inaccurate injection.

Thus, there is a need for a device for safely attaching and removing a needle assembly to/from a medicament delivery device.

SUMMARY

It is an object of the present invention to provide a needle assembly attachment and removal device for attaching a needle assembly to and removing the needle assembly from a medicament delivery device.

In an exemplary embodiment, a needle assembly attachment and removal device according to the present invention comprises a case having a base and a longitudinal axis, a carriage axially movable with the case from a first position to a second position, a carrier rotatably coupled to the carriage and adapted to hold a needle assembly, and a gearing arrangement rotatably coupled to the carriage and adapted to rotate the carrier in a first rotational direction as the carriage moves from the first position to the second position and in a second rotational direction as the carriage moves from the second position to the first position.

In an exemplary embodiment, the needle assembly attachment and removal device further comprises a retainer coupled to the case or the carriage or the carrier and adapted to align a medicament delivery device with the needle assembly.

In an exemplary embodiment, the base has a larger cross-section than the case.

In an exemplary embodiment, the needle assembly attachment and removal device further comprises a cap clamp coupled to the carrier and adapted to engage an outer cap of the needle assembly. The cap clamp includes resilient clamp arms adapted to engage a portion of the outer cap. The needle assembly attachment and removal device further comprises a push rod slidably coupled to the carriage, and a clamp ring coupled to the push rod and adapted to apply a compressive force on the clamp arms to maintain engagement with the portion of the outer cap. The push rod urges the clamp ring against the clamp arms when the push rod engages the base.

In an exemplary embodiment, the gearing arrangement includes a rack disposed in the case, and a pinion having a first gear face adapted to engage a gear wheel coupled to the carrier and a second gear face adapted to engage the rack. The rack is disposed at an angle relative to the longitudinal axis of the case, and the second gear face has a variable diameter. The gearing arrangement further includes a torsion spring applying a rotational biasing force to the pinion, and movement of the carriage from the first position to the second position causes the pinion to rotate and energize the torsion spring. The carriage rotates about the longitudinal axis and a rotational axis of the pinion is orthogonal to the longitudinal axis.

In an exemplary embodiment, the needle assembly attachment and removal device further comprises a compression spring adapted to engage a spring stop formed on the base. The compression spring is energized when the carriage is in the second position.

In an exemplary embodiment, the carriage includes a resilient pin adapted to engage a retaining groove in the case. As the carriage moves from the first position to the second position, the pin enters a first portion of the retaining groove and deflects toward a longitudinal axis of the case. When the pin engages a second portion of the retaining groove, the carriage is locked in the second position. When the pin is engaged in the second portion of the retaining groove, an axial force on the carriage directed toward the base causes the pin to disengage the second portion and enter a third portion of the retaining groove which allows the carriage to return to the first position. A force in the compression spring propels the carriage toward the first position when the pin enters the third portion of the retaining groove.

In an exemplary embodiment, the needle assembly attachment and removal device further comprises a clutch disposed between the cap clamp and the carrier. The clutch prevents rotation of the cap clamp relative to the carrier in the first rotational direction until a predetermined torque is applied on the outer cap. The clutch prevents rotation of the cap clamp relative to the carrier in the second rotational direction.

In an exemplary embodiment, the carriage includes guide wheels adapted to engage channels formed in the base.

In an exemplary embodiment the needle assembly attachment and removal device may be used with delivery devices such as injection pens (e.g. for re-usable or disposable Insulin or Heparin pens) and with all kinds of needle assemblies, such as pen needles.

The needle assembly attachment and removal device allows for an easy and safe mounting and demounting of needle assemblies onto a delivery device while preventing a user from needle stick injuries.

The needle assembly attachment and removal device allows the application of the proper torque to engage the needle assembly and the delivery device. This may avoid an unwanted disassembling of a cartridge holder from a body of the delivery device which may occur, if the torque for releasing the needle assembly is greater than the release torque of the cartridge holder.

The risk of human error when mounting the needle assembly is minimized. This results in a reduced risk for loose needles, destroyed threads caused by excessive torque or crossed threads. The risk of an obliquely-oriented needle is also eliminated.

The needle assembly attachment and removal device allow for single handed operation.

The needle assembly attachment and removal device may be adapted for screw-type mounting and demounting accessories in different applications which require frequent attachment and removal.

In an exemplary embodiment, the needle assembly attachment and removal device according to present invention further comprises a needle assembly engagement mechanism disposed on the retainer. The needle assembly engagement mechanism is adapted to selectively engage an outer cap of the needle assembly. The needle assembly engagement mechanism comprises a clip adapted to slide transversely relative to the retainer between an engagement position for engaging the outer cover and a disengagement position for disengaging the outer cover, a lever adapted to move the clip between the engagement position and the disengagement position, and a spring applying a biasing force on the lever to maintain the clip in the engagement position. The clip includes a partially circular rim that is adapted to engage the outer cover of the needle assembly in the engagement position. The lever is operably coupled to a button that is adapted to actuate the lever.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
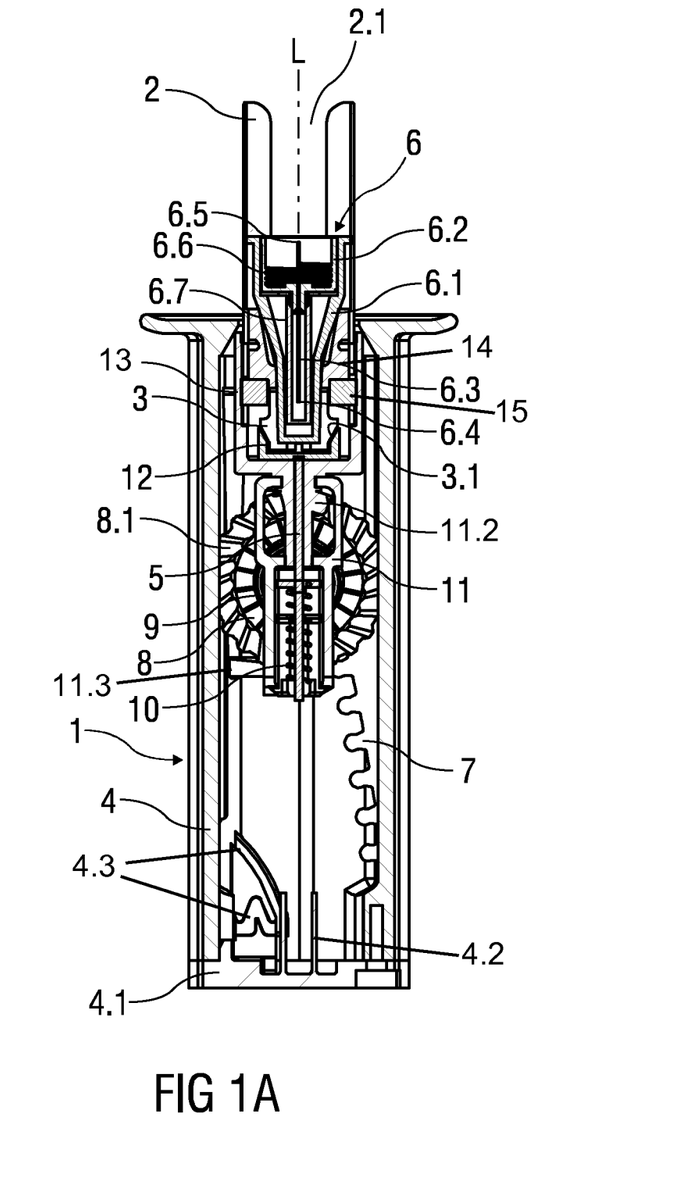
FIG. 1A is a longitudinal section of an exemplary embodiment of a needle assembly attachment and removal device in a first sectional plane.

FIG. 1A is a longitudinal section of a needle assembly attachment and removal device 1 in a first sectional plane according to an exemplary embodiment of the present invention. The device 1 is adapted to receive a medicament delivery device and to attach and remove a needle assembly 6 to and from the delivery device.

In an exemplary embodiment, the delivery device (not illustrated) may be any medicament delivery device including, but not limited to, a pen injector, an auto-injector, a safety syringe, etc. The delivery device may include a cartridge holder adapted to hold a medicament-containing cartridge (not illustrated). As understood by those of skill in the art, the delivery device may be a single-use device (e.g., the delivery device is disposed of after the cartridge is empty) or a re-usable device (e.g., the cartridge may be replaced when empty or otherwise necessary).

In an exemplary embodiment, the needle assembly includes a needle hub 6.2 adapted to engage the delivery device and a needle 6.3 which has a distal tip 6.4 and a proximal tip 6.5 coupled to the needle hub 6.2. The proximal tip 6.5 is arranged to pierce a septum of a cartridge in the delivery device when the needle assembly 6 is mounted to the delivery device, and the distal tip 6.4 is used to pierce an injection site. When the needle assembly 6 is coupled to the delivery device, the medicament can be displaced through a fluid channel within the needle 6.3.

In an exemplary embodiment, the needle hub 6.2 includes internal threads 6.6 for mating with threads formed on the delivery device. An inner needle cap 6.7 may be arranged over the needle 6.3. An outer cap 6.1 may be arranged over the needle hub 6.2, needle 6.3 and inner needle cap 6.7. The outer cap 6.1 may include features (e.g., grooves) which mate with corresponding features (e.g., ridges) on the needle hub 6.2, such that the outer cap 6.1 does not rotate relative to the needle hub 6.2 when they are engaged.

In an exemplary embodiment, the needle assembly attachment and removal device 1 comprises an elongate case 4 with a base 4.1 at a lower end. The base 4.1 may be planar to serve as a platform so that the device 1 may be placed on a surface during use. In an exemplary embodiment, the base 4.1 may be have a larger cross-section than the case 4 to increase surface area and stability when placed on a surface. In addition, an underside of the base 4.1 may include a coating or matting adapted to frictionally engage a surface. An upper end of the case 4 has an opening adapted to receive the needle assembly 6 and the delivery device.

In an exemplary embodiment, the device 1 includes a retainer 2 arranged on a carriage 11 which is slidably arranged within the case 4 along a longitudinal axis L. The retainer 2 may comprise a plurality of axial arms which have contoured internal surfaces adapted to support align the delivery device when it is inserted into the device 1. The retainer 2 may ensure that the delivery device properly engages/disengages the needle assembly 6 (e.g., that the threads are aligned correctly).

In an exemplary embodiment, the device 1 includes a carrier 13 rotatably coupled to the carriage 11. A cap clamp 14 may be rotatably coupled to the carrier 13 via a clutch 15 (which is keyed to the carriage 11). The cap clamp 14 is adapted to engage the outer cap 6.1 of the needle assembly 6. Resilient clamp arms 3 may be disposed at a lower end of the cap clamp 14. A clamp ring 12 is disposed in the carriage 11 and coupled to a push rod 5, which is slidably coupled to the carriage 11. The clamp ring 12 is adapted to engage the clamp arms 3 to push the clamp arms 3 into frictional engagement with the outer cap 6.1. The clamp arms 3 may include a tapered surface 3.1 adapted to engage a corresponding tapered surface of the clamp ring 12. The clamp arms 3 may deflect and frictionally engage the outer cap 6.1, as described further below.

In an exemplary embodiment, the clutch 15 includes a ratchet face adapted to engage a corresponding ratchet face on the cap clamp 14. As explained further below, the clutch 15 limits an attachment torque applied to the needle assembly 6 when the needle assembly 6 is mounted on the delivery device.

In an exemplary embodiment, a pinion 8 is rotatably coupled to the carriage 11 and may include a torsion spring 9 applying a biasing force to the pinion 8. The pinion includes a first gear face 8.1 which is adapted to mate with a gear wheel 11.2 on the carrier 13 and a second gear face 8.2 which is adapted to mate with a rack 7 formed in the case 4. Thus, rotation of the pinion 8 causes rotation of the carrier 13. In an exemplary embodiment, the rack 7 and the second gear face 8.2 form a rack and pinion arrangement having a variable transmission. The rack 7 may be arranged at an angle with respect to the longitudinal axis L so that a distance between the rack 7 and the longitudinal axis L increases along at least a portion of the length of the case 4 and is greatest near the base 4.1. To maintain engagement with the rack 7, the second gear face 8.2 has a variable diameter. Thus, when the carriage 11 is in or near the upper end of the case 4, translation of the carriage 11 causes low torque in the pinion 8 and high rotational speed, whereas translation near the low end of the case 4 causes an increase in torque and a lower rotational speed. The torsion spring 9 may bias the pinion towards the upper end of the case 4.

In an exemplary embodiment, the carriage 11 includes a compression spring 10 adapted to engage a spring stop 4.2 disposed on the base 4.1. The compression spring 10 compresses as the carriage 11 moves toward the base 4.1.

In an exemplary embodiment, the carriage 11 includes a pin 11.3 adapted to engage a retaining groove 4.3 formed adjacent the base 4.1. As explained further below, the retaining groove 4.3 may include various positions for the pin 11.3 to maintain the carriage 11 in a position relative to the case 4.

Figure 1B:
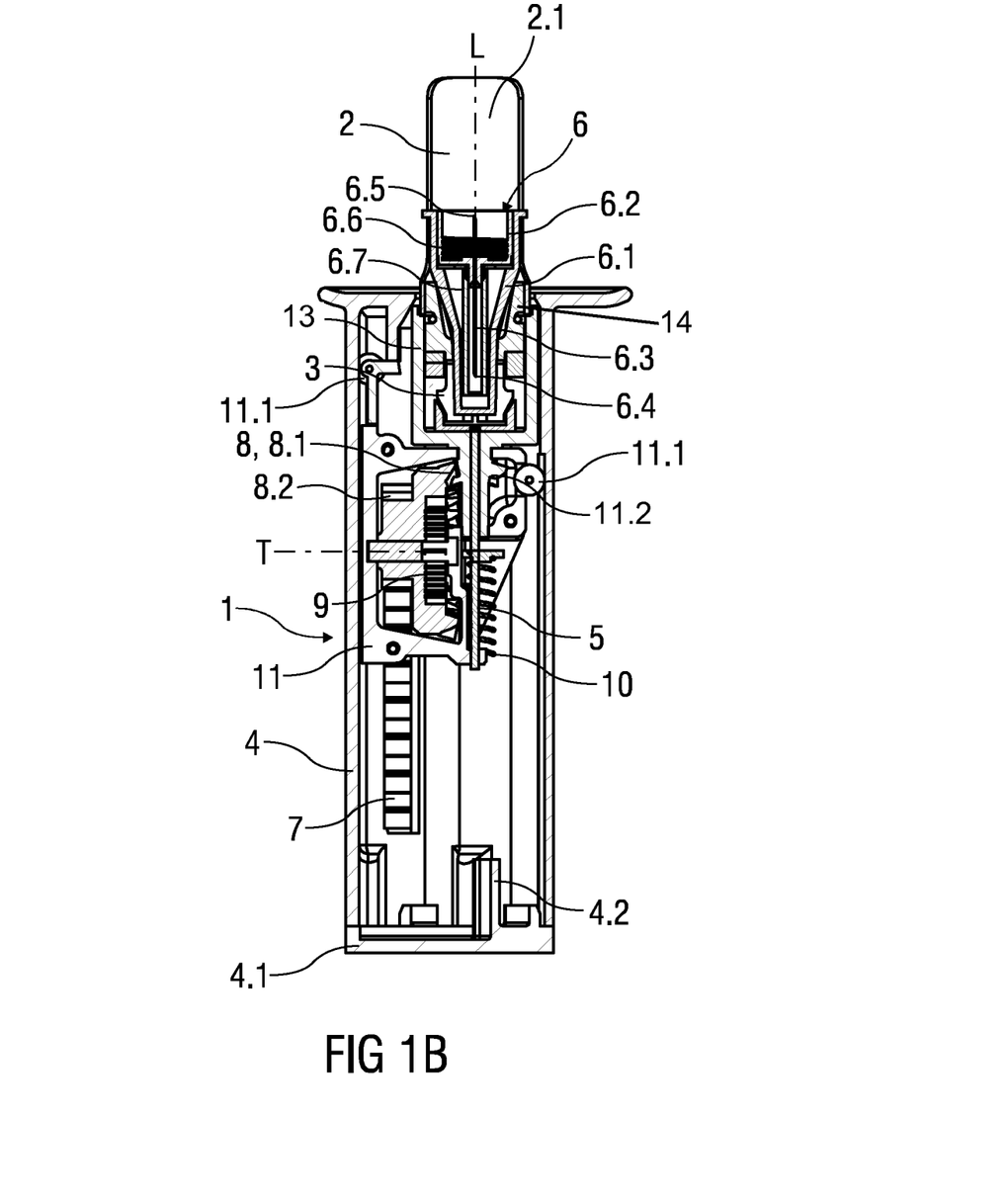
FIG. 1B is a longitudinal section of an exemplary embodiment of a needle assembly attachment and removal device in a second sectional plane, FIG. 2 a longitudinal section of an exemplary embodiment of a needle assembly attachment and removal device in a third sectional plane.

As shown in FIG. 1B, the carriage 11 may include one or more guide wheels 11.1 adapted to engage one or more corresponding channels in the case 4 for facilitating the axial movement of the carriage 11 relative to the case 4 and for maintaining an angular position of the carriage 11 relative to the case 4.

Figure 2:
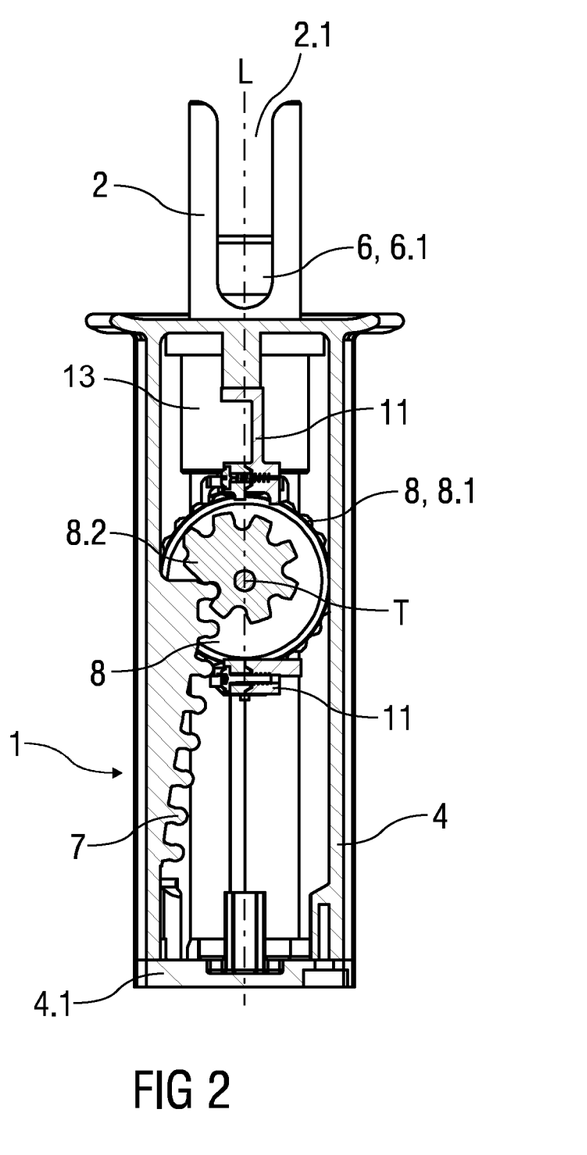

FIGS. 1A, 1B and 2 show the device 1 in a pre-use state, in which the carriage 11 is in a first axial position relative to the case 4. In an exemplary embodiment, the needle assembly 6 may be placed in the device 1 such that the outer cap 6.1 of the needle assembly 6 engages the cap clamp 14. As the needle assembly 6 is pushed into the cap clamp 14, the cap arms 3 may frictionally engage the outer cap 6.1 and/or the clamp ring 12 may prevent the cap arms 3 from deflecting and ensure a frictional hold on the outer cap 6.1.

To mount the needle hub 6.2 onto the delivery device, the delivery device is aligned with the needle aperture 2.1 of the retainer 2, and the retainer 2 aligns the delivery device with the needle hub 6.2 in the needle assembly. As the delivery device is pressed into the device 1, the carriage 11 translates towards the base 4.1. Because the second gear face 8.2 engages the rack 7 and because the first gear face 8.1 engages the gear wheel 11.2, the carrier 13 rotates in a first rotational direction as the carriage 11 translates axially. As the carrier 13 rotates, the cap clamp 14 (and outer cap 6.1 and needle hub 6.2) rotate in the first rotational direction so that the threads 6.6 on the needle hub 6.2 engage the threads on the delivery device. Due to the increasing diameter of the second gear face 8.2, the torque applied to the needle hub 6.2 increases as the carriage 11 translates towards the base 4.1. As the carriage 11 translates towards the base 4.1 and the pinion 8 rotates, the torsion spring 9 is energized.

When the carriage 11 is proximate the base 4.1, the pin 11.3 engages the retaining groove 4.3. The retaining groove 4.3 may have a first portion which is adapted to receive the pin 11.3 and deflect the pin 11.3 toward the longitudinal axis L. The compression spring 10 engages and compresses against the spring stop 4.2. The push rod 5 abuts the base 4.1 and further translation of the carriage 11 causes the clamp ring 12 to engage the clamp arms 3 to secure the outer cap 6.1 in the cap clamp 14.

After the needle hub 6.2 has been properly secured to the delivery device, any further rotation of the carrier 13 relative to the needle hub 6.2 may cause the clutch 15 to disengage the cap clamp 14. Thus, the clutch 15 prevents overtightening the needle hub 6.2. When the clutch 15 disengages the cap clamp 14, an audible feedback (e.g., clicking of the slipping ratchet faces) may be provided to indicate that the needle hub 6.2 has been secured to the delivery device.

Figure 3:
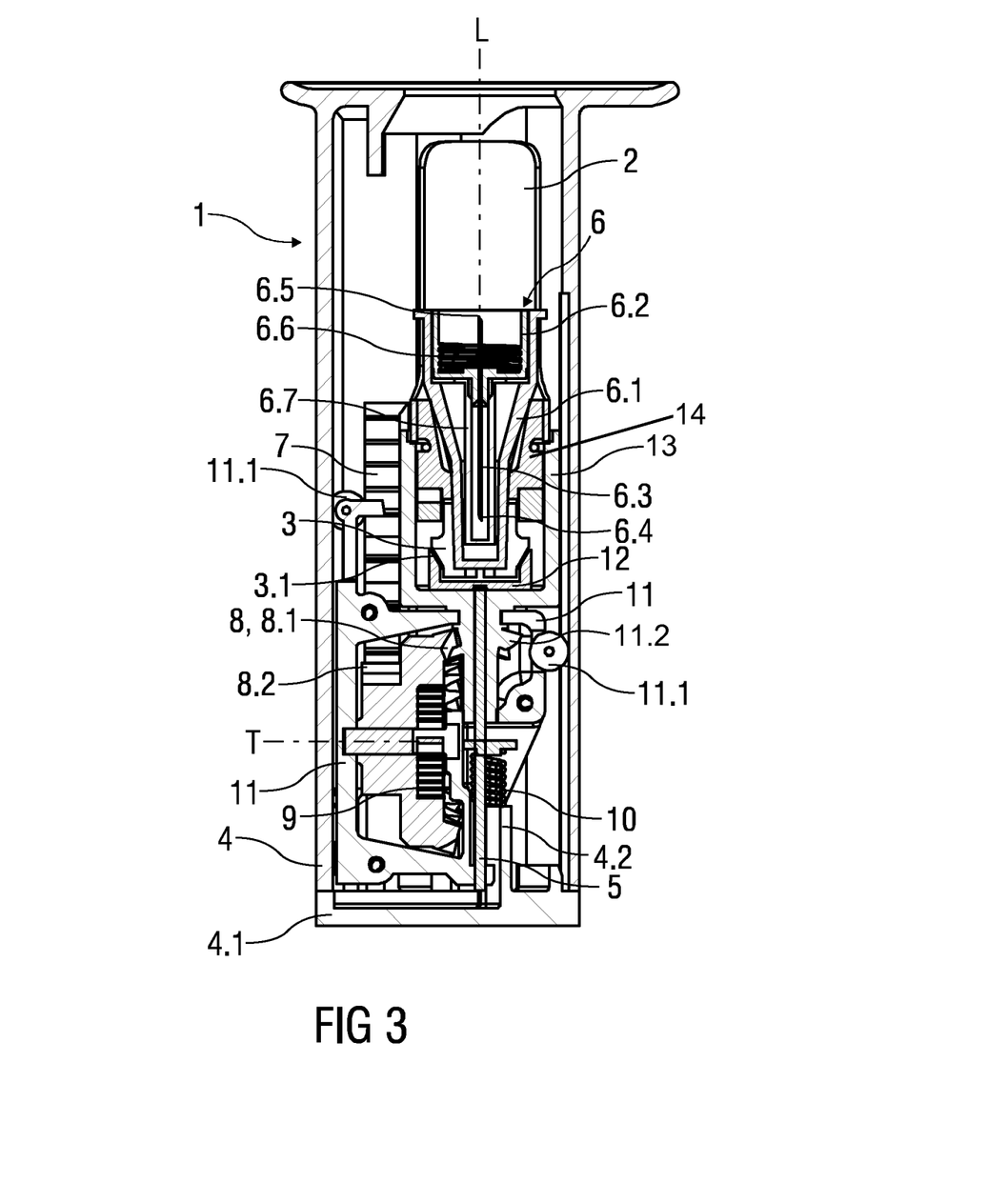
FIG. 3 is a longitudinal section of an exemplary embodiment of a needle assembly attachment and removal device in the second sectional plane with a carriage in a depressed position.

As shown in FIG. 3, when the delivery device (with the needle hub 6.2 attached thereto) is removed from the device 1, the carriage 11 is in a second axial position. The clamp arms 3 and/or the clamp ring 12 may hold the outer cap 6.1 in the device 1, and the force in the torsion spring 9 and/or the force in the compression spring 10 may push the carriage 11 away from the base 4.1. Due to the resilient force on the pin 11.3, the pin 11.3 moves to a second (locking) portion in the retaining groove 4.3. When the pin 11.3 is in the second portion, the carriage 11 is prevented from further axial movement away from the base 4.1.

After an injection, the device 1 may be used to remove the used needle hub 6.2. The delivery device may be reinserted into the device 1 by aligning with the retainer 2. A first tactile feedback (e.g., increased resistance) may be provided when the needle hub 6.2 engages the outer cap 6.1. When the delivery device is advanced into the device 1 and the needle hub 6.2 engages the outer cap 6.1, the carriage 11 may be advanced toward the base 4.1 a small distance, and the pin 11.3 may disengage the second portion in the retaining groove 4.3 and resiliently deflect into a third portion, which may be a channel that does not obstruct axial movement of the pin 11.3 and allows the carriage 11 to translate axially away from the base 4.1. The force in the torsion spring 9 rotates the pinion 8 to climb up the rack 7, and the force in the compression spring 10 pushes the carriage 11 away from the base 4.1. The rotation of the pinion 8 results in rotation of the carrier 13 in a second rotational direction which disengages the needle hub 6.2 from the delivery device.

In an exemplary embodiment, the compression spring 10 is primarily active in a first part of a demounting cycle, e.g., to generate high torque and high rotational speed on the carrier 13 and the cap clamp 14 to loosen the thread 6.6 of the needle hub 6.2 from the threads on the delivery device. After the carriage 11 has travelled a distance relative to the case 4, the push rod 5 no longer abuts the base 4.1 and the compression spring 10 disengages the spring stop 4.2. The remaining rotational force on the carriage 11 is supplied by the torsion spring 9. After the needle hub 6.2 has been loosened from the delivery device, the torque of the torsion spring 9 suffices to return the delivery device to the initial upper end position and unscrew the needle hub 6.2 from the delivery device.

After the needle hub 6.2 has disengaged the delivery device and the carriage 11 returns to its initial position, the needle assembly 6 may be grasped and removed from the device 1 for disposal.

In an exemplary embodiment, the device 1 may include a locking mechanism (not shown) for locking the carriage 11 relative to the case 4. For example, the locking mechanism may be a lever which locks the carriage 11 in a position (e.g., the second position) relative to the case 4 or a cover disposed over the needle aperture 2.1.

Figure 4:
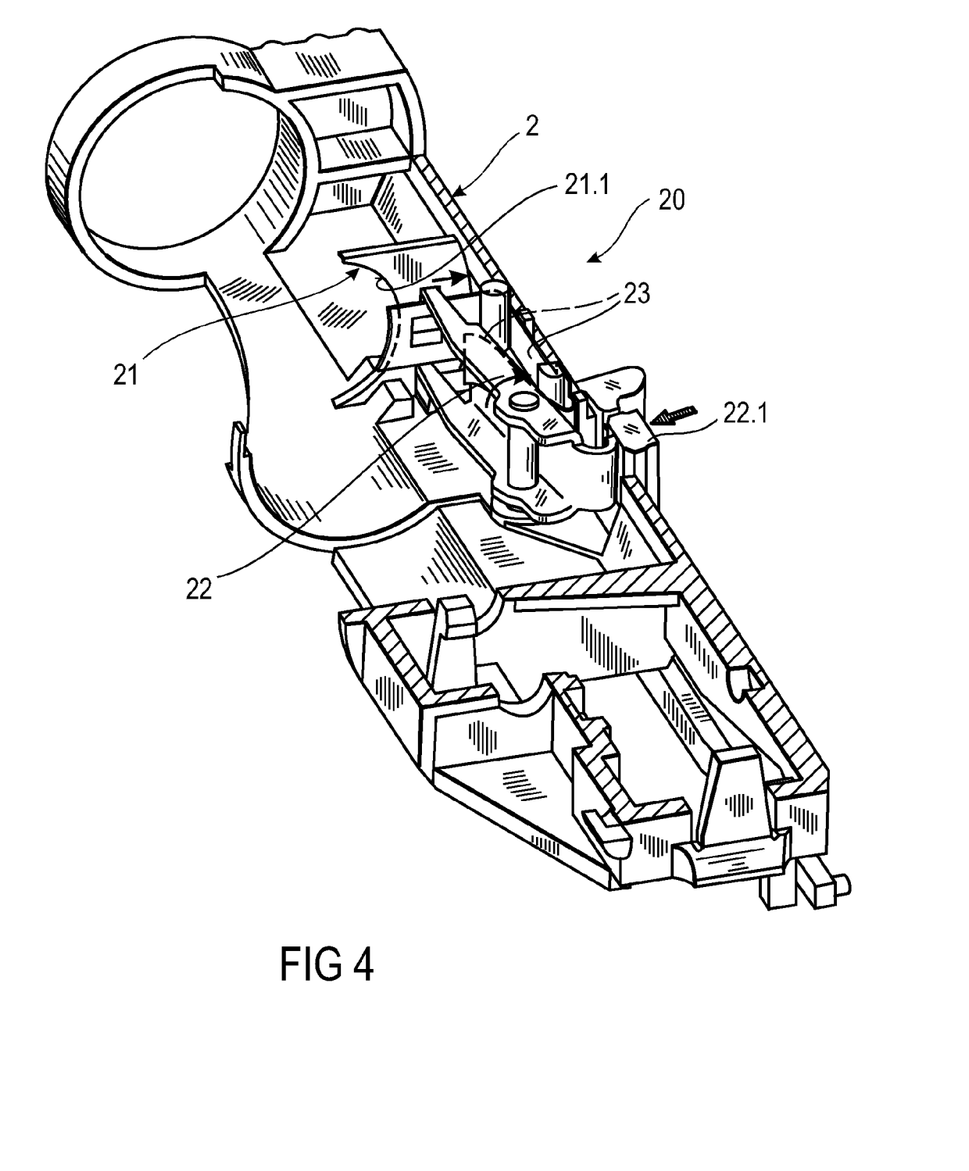
FIG. 4 is a perspective view of an exemplary embodiment of a needle assembly engagement mechanism for a needle assembly attachment and removal device.

In an exemplary embodiment, as shown in FIG. 4, the device 1 may include a needle assembly engagement mechanism 20 which is adapted to engage the needle assembly 6 during use of the device 1 and selectively disengage the needle assembly 6 for removal from the device 1. The needle assembly engagement mechanism 20 may be formed on the retainer 2 and/or the carriage 11. In an exemplary embodiment, the needle assembly engagement mechanism 20 comprises a clip 21 tranversely slidable relative to the retainer 2 between an engagement position and a disengagement position. The clip 21 is actuated by a lever 22 that is biased by a spring 23 (e.g., a leaf spring). The clip 21 may have a partially circular rim 21.1 which may have a ramped proximal surface adapted to engage the outer cover 6.1 of the needle assembly 6. Thus, when the needle assembly 6 is placed in the device 1, the rim 21.1 abuts the outer cover 6.1, and the clip 21 is displaced transversely from the engagement position to the disengagement position. Displacement of the clip 21 pushes the lever 22 against the biasing force of the spring 23, until the outer cover 6.1 bypasses the rim 21.1, at which point the rim 21.1 returns to the engagement position, abutting a proximal surface of the outer cap 6.1. The clip 21 then maintains the outer cover 6.1 within the carrier 13.

When a used needle assembly 6 is in the outer cover 6.1 and is going to be removed from the device 1, a button 22.1 coupled to the lever 22 can be pressed to disengage the clip 21 from the outer cap 6.1. The button 22.1 may be formed integrally with the lever 22 or be a separate component which is adapted to engage the lever 22. Pressing the button 22.1 actuates the lever 22 against the biasing force of the spring 23 and displaces the clip 21 transversely from the engagement position to the disengagement position. The used needle assembly 6 in the outer cover 6.1 can then be removed manually, or the device 1 can be turned upside-down and the used needle assembly 6 in the outer cover 6.1 will slide out of the device 1.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle assembly attachment and removal device comprising:
   a case having a base and a longitudinal axis;
   a carriage axially movable with the case from a first position to a second position;
   a carrier rotatably coupled to the carriage and adapted to hold a needle assembly;
   a gearing arrangement rotatably coupled to the carriage and adapted to rotate the carrier in a first rotational direction as the carriage moves from the first position to the second position and in a second rotational direction as the carriage moves from the second position to the first position; and
   a cap clamp coupled to the carrier and adapted to engage an outer cap of the needle assembly, wherein the cap clamp includes resilient clamp arms adapted to engage a portion of the outer cap.

2. The needle assembly attachment and removal device according to claim 1, further comprising:
   a retainer coupled to the case or the carriage or the carrier and adapted to align a medicament delivery device with the needle assembly.

3. The needle assembly attachment and removal device according to claim 2, further comprising:
   a needle assembly engagement mechanism disposed on the retainer, the needle assembly engagement mechanism adapted to selectively engage an outer cap of the needle assembly.

4. The needle assembly attachment and removal device according to claim 1, wherein the base has a larger cross-section than a remainder of the case.

5. The needle assembly attachment and removal device according to claim 1, further comprising:
   a push rod slidably coupled to the carriage; and
   a clamp ring coupled to the push rod and adapted to apply a compressive force on the clamp arms to maintain engagement with the portion of the outer cap, wherein the push rod urges the clamp ring against the clamp arms when the push rod engages the base.

6. The needle assembly attachment and removal device according to claim 1, wherein the gearing arrangement includes:
   a rack disposed in the case; and
   a pinion having a first gear face adapted to engage a gear wheel coupled to the carrier and a second gear face adapted to engage the rack.

7. The needle assembly attachment and removal device according to claim 6, wherein the rack is disposed at an angle relative to the longitudinal axis of the case, and the second gear face has a variable diameter.

8. The needle assembly attachment and removal device according to claim 1, further comprising:
   a compression spring adapted to engage a spring stop formed on the base, the compression spring being energized when the carriage is in the second position.

9. The needle assembly attachment and removal device according to claim 1, wherein the carriage includes a resilient pin adapted to engage a retaining groove in the case, wherein as the carriage moves from the first position to the second position, the pin enters a first portion of the retaining groove and deflects toward a longitudinal axis of the case, and wherein when the pin engages a second portion of the retaining groove, the carriage is locked in the second position, and wherein when the pin is engaged in the second portion of the retaining groove, an axial force on the carriage directed toward the base causes the pin to disengage the second portion and enter a third portion of the retaining groove which allows the carriage to return to the first position.

10. The needle assembly attachment and removal device according to claim 9, wherein a force in a compression spring propels the carriage toward the first position when the pin enters the third portion of the retaining groove.

11. The needle assembly attachment and removal device according to claim 1, further comprising:
   a clutch disposed between the cap clamp and the carrier, the clutch preventing rotation of the cap clamp relative to the carrier in the first rotational direction until a predetermined torque is applied on the outer cap, and preventing rotation of the cap clamp relative to the carrier in the second rotational direction.

12. The needle assembly attachment and removal device according to claim 1, wherein the carriage includes guide wheels adapted to engage channels formed in the base.

13. A needle assembly attachment and removal device comprising:
   a case having a base and a longitudinal axis;
   a carriage axially movable with the case from a first position to a second position;
   a carrier rotatably coupled to the carriage and adapted to hold a needle assembly;
   a gearing arrangement rotatably coupled to the carriage and adapted to rotate the carrier in a first rotational direction as the carriage moves from the first position to the second position and in a second rotational direction as the carriage moves from the second position to the first position;
   wherein the gearing arrangement further includes
      a rack disposed in the case at an angle relative to the longitudinal axis of the case,
      a pinon having a first gear face adapted to engage a gear wheel coupled to the carrier and a second gear face adapted to engage the rack, the second gear face having a variable diameter, and
      a torsion spring applying a rotational biasing force to the pinion, wherein movement of the carriage from the first position to the second position causes the pinion to rotate and energize the torsion spring.

14. The needle assembly attachment and removal device according to claim 13, wherein the carriage rotates about the longitudinal axis and a rotational axis of the pinion is orthogonal to the longitudinal axis.

15. The needle assembly attachment and removal device according to claim 13, wherein the base has a larger cross-section than a remainder of the case.

16. The needle assembly attachment and removal device according to claim 13, further comprising:
   a compression spring adapted to engage a spring stop formed on the base, the compression spring being energized when the carriage is in the second position.

17. A needle assembly attachment and removal device comprising:
   a case having a base and a longitudinal axis;
   a carriage axially movable with the case from a first position to a second position;
   a carrier rotatably coupled to the carriage and adapted to hold a needle assembly;
   a gearing arrangement rotatably coupled to the carriage and adapted to rotate the carrier in a first rotational direction as the carriage moves from the first position to the second position and in a second rotational direction as the carriage moves from the second position to the first position;
   a retainer coupled to the case or the carrier or the carrier and adapted to align a medicament delivery device with the needle assembly; and
   a needle assembly engagement mechanism disposed on the retainer, the needle assembly engagement mechanism being adapted to selectively engage an outer cap of the needle assembly and comprising:
      a clip adapted to slide transversely relative to the retainer between an engagement position for engaging the outer cap and a disengagement position for disengaging the outer cap;
      a lever adapted to move the clip between the engagement position and the disengagement position; and
      a spring applying a biasing force on the lever to maintain the clip in the engagement position.

18. The needle assembly attachment and removal device according to claim 17, wherein the clip includes a partially circular rim that is adapted to engage the outer cap of the needle assembly in the engagement position.

19. The needle assembly attachment and removal device according to claim 17, wherein the lever is operably coupled to a button that is adapted to actuate the lever.

20. The needle assembly attachment and removal device according to claim 17, wherein the base has a larger cross-section than a remainder of the case.

* * * * *